United States Patent [19]

Finch et al.

[11] Patent Number: 5,221,695

[45] Date of Patent: Jun. 22, 1993

[54] AQUEOUS FORMULATION CONTAINING A PIPERIDINYLCYCLOPENTYLHEPTENOIC ACID DERIVATIVE AND BETA-CYCLODEXTRIN

[75] Inventors: Harry Finch, Letchworth; Anthony J. Phillips, Saffron Walden, both of England

[73] Assignee: Glaxo Group Limited, London, United Kingdom

[21] Appl. No.: 895,038

[22] Filed: Jun. 8, 1992

Related U.S. Application Data

[63] Continuation of Ser. No. 598,148, Oct. 16, 1990, abandoned, which is a continuation of Ser. No. 287,290, Dec. 21, 1988, abandoned.

[30] Foreign Application Priority Data

Dec. 22, 1987 [GB] United Kingdom ............... 8729823
Feb. 25, 1988 [GB] United Kingdom ............... 8804422

[51] Int. Cl.$^5$ .................. A61K 47/00; A61K 31/215; A61K 31/445; A61K 31/715
[52] U.S. Cl. ..................................... 514/777; 514/58; 514/59; 514/317; 514/530; 514/531; 514/778
[58] Field of Search .............. 514/58, 59, 530, 531, 514/777, 778, 317

[56] References Cited

U.S. PATENT DOCUMENTS

| | | | |
|---|---|---|---|
| 4,447,428 | 5/1988 | Collington et al. | 514/317 |
| 4,623,641 | 11/1986 | Szejtli et al. | 514/58 |
| 4,826,963 | 5/1989 | Szoke et al. | 536/103 |
| 4,977,163 | 12/1990 | Collington et al. | 514/317 |
| 4,983,586 | 1/1991 | Bodor | 514/58 |
| 5,068,227 | 11/1991 | Weinshenker | 514/777 |

FOREIGN PATENT DOCUMENTS

| | | |
|---|---|---|
| 0256805 | 8/1987 | European Pat. Off. |
| 7426416 | 7/1974 | Japan . |
| 56-150039 | 11/1981 | Japan . |
| 185072 | 8/1987 | Japan . |
| 1351238 | 9/1974 | United Kingdom . |
| 1411065 | 1/1975 | United Kingdom . |
| 1419221 | 4/1975 | United Kingdom . |
| 2097397 | 11/1982 | United Kingdom . |
| 2127406 | 4/1984 | United Kingdom . |
| WO85/02767 | 6/1985 | World Int. Prop. O. |
| WO86/04504 | 2/1986 | World Int. Prop. O. |

OTHER PUBLICATIONS

Abstract in English of Polish Patent No. 136,829.
Chemical & Pharmaceutical Bulletin, vol. 28 No. 7, 1975–1980 (1980).
J. Pharm. Sci. 67 (12), 1665-8 (1978).
J. Szejtli, *Controlled Drug Bioavailability*, Chapter 8 titled "Molecular Entrapment and Release Properties of Drugs by Cyclodextrins", pp. 365-421.
"Cyclodextrins and Their Inclusion Compounds with Drugs", Russian Translation—Khim. Farm. Zh 20, No. 5,525-32 (1986).
Derwent Abstracts (103 abstracts of patents).
Chemical Abstracts, vol. 81, No. 10, 54460r, p. 324, 1974.
Chemical Abstracts, vol. 103; 179894q, p. 94, 1985.
Chemical Abstracts, vol. 102; 26774e, p. 122, 1984.
Chemical Abstracts, vol. 110; 50452j, 1989.

*Primary Examiner*—Frederick E. Waddell
*Assistant Examiner*—K. Weddington
*Attorney, Agent, or Firm*—Bacon & Thomas

[57] ABSTRACT

Aqueous formulations comprising [1R-[1α(Z),2β,3β,-5α]]-(+)-7-[5-[[(1,1'-biphenyl)-4-yl]methoxy]-3-hydroxy-2-(1-piperidinyl) cyclopentyl]-4-heptenoic acid or its hydrochloride salt and an unsubstituted or substituted α-, β- or γ-cyclodextrin have been found which are particularly useful in the treatment or prophylaxis of conditions mediated by thromboxane $A_2$. Suitable aqueous formulations include injections, oral preparations such as syrups and capsules and inhalation preparations.

3 Claims, No Drawings

AQUEOUS FORMULATION CONTAINING A PIPERIDINYLCYCLOPENTYLHEPTENOIC ACID DERIVATIVE AND BETA-CYCLODEXTRIN

This application is a continuation of application no. 07/598,148 filed Oct. 16, 1990, now abandoned, which is a continuation of application no. 07/287,290 filed Dec. 21, 1988, now abandoned.

This invention relates to aqueous formulations containing as active ingredient [1R-[1α(Z), 2β,3β,5α]]-(+)-7-[5-[[(1,1'-biphenyl)-4-yl]methoxy]-3-hydroxy-2-(1-piperidinyl)cyclopentyl]-4-heptenoic acid (hereinafter referred to as 'Compound A'), to processes for their preparation and to their use in medicine.

Compound A is described in our British Patent No. 2097397 as one of a group of aminocyclopentane derivatives having endoperoxide and thromboxane antagonist activity, and it is reported therein that such compounds are of interest in the treatment of asthma and cardiovascular diseases. More recently, we discovered that the hydrochloride salt of Compound A has advantages over Compound A and other salts and solvates thereof both in its preparation and in its use in medicine. The hydrochloride salt is described in our British Patent No. 2127406.

Compound A is unfortunately only sparingly soluble in water and formulations in water containing the hydrochloride salt of Compound A together with standard excipients and/or carriers have proved to be unacceptable for intravenous administration as the hydrochloride salt of Compound A is converted to the virtually insoluble Compound A at near to physiological pH.

We have now found that the solubility in water of Compound A or its hydrochloride salt at around physiological pH is significantly improved in the presence of an unsubstituted or substituted α-, β- or γ-cyclodextrin (or a hydrate thereof). We have also found that aqueous formulations comprising Compound A or the hydrochloride salt thereof and an unsubstituted or substituted α-, β- or γ-cyclodextrin (or a hydrate thereof) are suitable for use in medicine, more particularly for use in the treatment or prophylaxis of conditions mediated by thromboxane $A_2$, when administered either orally, by inhalation or parenterally, in particular by injection (e.g. intravenously).

Thus, according to one aspect of the present invention, we provide an aqueous formulation comprising Compound A or the hydrochloride salt thereof with an unsubstituted or substituted α-, β-, or γ-cyclodextrin (or a hydrate thereof).

In another aspect of the invention, we provide an aqueous formulation as defined herein for use in medicine, more particularly for use in the treatment or prophylaxis of conditions mediated by thromboxane $A_2$.

According to another aspect of the invention, we provide a method of treating conditions mediated by thromboxane $A_2$ which method comprise administering to the human or animal patient an effective amount of Compound A in an aqueous formulation as defined herein.

Suitable conditions which may be treated with aqueous formulations of the present invention include those conditions described in British Patents Nos. 2097397 and 2127406 treated using other (e.g. oral) formulations of Compound A and the hydrochloride salt of Compound A respectively. In particular, the aqueous formulations of the present invention may be used in the treatment or prophylaxis of occlusive vascular disease, including myocardial infarction, cardiac fatalities, unstable angina, transient ischaemic attacks and cerebral infarction, atherosclerosis and vessel wall disease, peripheral vascular disease, retinopathy, postoperative thrombosis and pulmonary embolism. The aqueous formulations may also be used in the prophylaxis of peri- and postoperative complications following organ transplantation (particularly cardiac and renal), coronary artery bypass, peripheral artery bypass and thrombolysis. The aqueous formulations are also of potential use in connection with peptic ulcer disease, more particularly for the prevention of relapse of healed peptic ulcers.

Preferably, in the aqueous formulations of the present invention Compound A is used as its hydrochloride salt.

It will be appreciated by those skilled in the art that the benefits of the present invention may be achieved by utilising more than one cyclodextrin, although the use of a single cyclodextrin is generally preferred.

Where a substituted cyclodextrin is employed any suitable substituted cyclodextrin known in the art may be used according to the present invention. Suitable substituted cyclodextrins for use according to the present invention will be readily appreciated by persons skilled in the art and will include sulphur-containing cyclodextrins, nitrogen-containing cyclodextrins, alkylated (e.g. methylated) cyclodextrins such as mono-, di- or trimethylated derivatives of a cyclodextrin (e.g. of β-cyclodextrin) and hydroxyalkyl (e.g. hydroxypropyl) cyclodextrins such as hydroxypropyl β-cyclodextrin and acylated derivatives thereof. Hydroxyalkyl (e.g. hydroxypropyl) cyclodextrins such as hydroxypropyl β-cyclodextrin have been found to be particularly suitable for use according to the present invention.

Conveniently a single unsubstituted cyclodextrin is employed according to the present invention. Particularly preferred is β-cyclodextrin, conveniently used in its hydrated form.

In order for the aqueous formulation to exhibit the desired properties it is important that the correct molar ratio of Compound A or its hydrochloride salt to the cyclodextrin(s) is used. We have found a molar ratio of Compound A or its hydrochloride salt to the cyclodextrin(s) within the range 1:1 to 1:4 to be suitable.

It will be appreciated by persons skilled in the art that the aqueous formulations of the present invention may, if desired, also contain one or more pharmaceutical carriers or excipients. Suitable excipients which may be incorporated into the aqueous formulation include agents to make the preparation isotonic with blood plasma (e.g. sodium chloride, dextrose or preferably mannitol) and buffering agents (e.g. phosphate buffer or a mixture of sodium acid phosphate and disodium phosphate).

The aqueous formulations of the present invention are particularly suitable for parenteral administration in particular by injection (e.g. intravenously). When presented for parenteral administration it is desirable that the formulation is at about physiological pH. It may therefore be appropriate to adjust the pH to about physiological pH using conventional means, for example using a suitable base such as a hydroxide (e.g. an alkali metal hydroxide such as sodium hydroxide solution). Conveniently, the pH is adjusted to about pH 6.0.

For parenteral administration, in particular for administration by injection (e.g. intravenously), it is highly desirable for the formulation to be presented as a clear solution. A clear solution requires no further processing (e.g. constitution of a dry powder) and may be administered without delay. The use of a clear solution also ensures that the product can be easily inspected for particulate or other visible contamination. Furthermore, intravenous injection of an aqueous solution of a drug can produce an immediate physiological action. We have found that at least one mole of the cyclodextrin must be used for every one mole of the hydrochloride of Compound A in order to obtain a clear solution at near to physiological pH at normal storage temperatures, and in the case of $\beta$-cyclodextrin at least about 1.2 moles must be used.

In a preferred embodiment of the present invention, therefore, we provide a clear aqueous formulation comprising the hydrochloride salt of Compound A and $\beta$-cyclodextrin (or a hydrate thereof), at about physiological pH wherein the formulation contains at least about 1.2 moles of $\beta$-cyclodextrin (e.g. 1.2 to 2 moles) for every one mole of the hydrochloride salt of Compound A. Preferably the molar ratio will be about 1:1.4.

The concentration of Compound A or the hydrochloride salt thereof in the aforementioned aqueous formulations suitable for parenteral administration, in particular for administration by injection (e.g. intravenously), is conveniently within the range 0.1-10 mg/ml, e.g. 0.1-5 mg/ml, expressed as the free base. Preferably, the concentration is 1 mg/ml expressed as the free base when the aqueous formulation is administered by intravenous injection. If desired, a higher concentration may be used and the solution may be diluted prior to use with, for example, an isotonic saline solution or dextrose or mannitol solution. Conveniently, solutions suitable for injection are presented in an appropriate dose volume (e.g. 1-100 ml). Dilutions suitable for continuous infusion may have a concentration of Compound A or its hydrochloride salt of 0.01-0.2 mg/ml expressed as the free base. The solution for continuous infusion may be presented in this form, for example in packs of 50-100 ml, or may be presented in more concentrated forms for subsequent dilution before use with, for example, an isotonic saline solution or dextrose or mannitol solution. Alternatively, small volumes of a more concentrated solution (e.g. 0.1-5 mg/ml) may be utilised for continuous infusion conveniently administered at a rate of 0.5 to 9.9 ml/h.

The aqueous formulations described herein may conveniently be prepared by mixing Compound A or, more preferably, its hydrochloride salt with the remaining constituents in water. Preferably, Compound A or its hydrochloride salt are dissolved in water and the remaining constituents are added thereto. For parenteral administration, in particular by injection (e.g. intravenously), the bulk solution is preferably filtered, then filled into suitable containers and terminally sterilised, for example by heating. Alternatively, the solution may be sterilised by filtration and then aseptically filled into suitable containers.

It will be appreciated that water suitable for injection will be used when the parenteral formulation is to be administered intravenously or by continuous infusion.

Formulations for injection may be presented in unit dose form in suitable containers such as ampoules, vials or pre-filled syringes, or in multi-dose containers with an added preservative.

As stated hereinbefore, the aqueous formulations of the present invention are also suitable for oral administration (e.g. as a capsule, syrup or solution) or for administration by inhalation (e.g. as an aerosol spray conveniently presented as a nebuliser). British Patent Nos. 2097397 and 2127406 provide suitable general methods for the preparation of oral and inhalation formulations which may be readily adapted without undue experimentation for present purposes.

Aqueous formulations may also be prepared by dissolving a solid cyclodextrin complex of Compound A or its hydrochloride salt in water together, where desirable, with one or more other constituents as defined above.

Thus, in a further aspect of the present invention, we provide an aqueous formulation comprising a complex of Compound A or the hydrochloride salt thereof and a cyclodextrin.

In another aspect of the invention, we provide a complex of Compound A or its hydrochloride salt and a cyclodextrin. The ratio of Compound A or the hydrochloride salt of Compound A with the cyclodextrin in the said complex will, of course, vary considerably depending on the cyclodextrin used and the conditions employed for preparing the complex. However, we have found a molar ratio of Compound A or its hydrochloride salt with the cyclodextrin within the range 1:1 to 1:3 to be suitable.

The cyclodextrin employed in the solid complex may be unsubstituted or substituted $\alpha$-, $\beta$- or $\gamma$-cyclodextrin as defined previously or may be a mixture of such cyclodextrins (e.g. a mixture of two such cyclodextrins). Preferably $\gamma$-cyclodextrin or, more preferably, $\beta$-cyclodextrin is employed.

In a particular aspect of the present invention we provide a complex of Compound A and $\beta$-cyclodextrin in which the molar ratio of Compound A to $\beta$-cyclodextrin is within the range 1:1 to 1:2, and is preferably about 1:1.

In another particular aspect of the present invention we provide a complex of Compound A and $\gamma$-cyclodrextrin in which the molar ratio of Compound A to $\gamma$-cyclodextrin is about 1:1.5.

Complexes of Compound A or the hydrochloride salt thereof and cyclodextrin may be prepared by mixing Compound A or its hydrochloride salt with the cyclodextrin(s) or a hydrate thereof in a suitable solvent under conditions whereby the desired complex is formed. Thus, for example, the complexes may be prepared by dissolving Compound A or it hydrochloride salt in water or an organic solvent which is miscible with water (e.g. an alcohol such as methanol) and adding to the solution a solution of the appropriate cyclodextrin(s) or a hydrate thereof in water and/or an organic solvent which is miscible with water. The reaction may be effected at a temperature in the range of 0° to 80° C.; however the mixture is preferably kept at around room temperature and the desired complex obtained by concentrating the mixture under reduced pressure or by allowing the mixture to cool. The mixing ratio of organic solvent with water may vary considerably according to the solubilities of the starting materials and products. Preferably 1 to 4 moles of cyclodextrin are used for each mole of Compound A or its hydrochloric salt.

The resulting complexes may be obtained as white solids with high thermal stability and good water solubility. Such physical characteristics make them particularly suitable for formulation into pharmaceutical preparations for medical use. In addition to the aforementioned aqueous formulations of complexes of Compound A or its hydrochloride salt and cyclodextrin suitable particularly for parenteral administration, the complexes may also be formulated for oral or parenteral administration or for administration by inhalation according to the general methods described in British Patent Nos. 2097397 and 2127406.

An appropriate daily dose regime for Compound A or its hydrochloride salt when employed in one of the formulations of the present invention will, of course, depend on the specific condition to be treated, the age and condition of the patient and the route of administration. However, generally the dosages quoted in British Patent Nos. 2097397 and 2127406 will be suitable.

The following examples are included by way of illustrating the present invention and should not be construed as a limitation of the invention. In the following examples the molar ratios were determined by $^1$H N.M.R. analysis and all temperatures are in °C.

EXAMPLE 1

(a)

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoate: β-cyclodextrin (1:1) complex β-Cyclodextrin hydrate (0.954 g) was nearly completely dissolved in water (35 ml). The suspension was filtered and the filtrate added to a solution of Compound A (0.2 g, Example 10 in GB-B-2097397) in methanol (10 ml). The reaction solution was stirred at 21° for 26 h to give a clear solution which was evaporated to a volume of 12 ml when slight crystallisation began to occur. The suspension was cooled to 5° for 1 h to produce a thick precipitate which was filtered off and dried to give the title compound (0.273 g), m.p.>310°, darkens above 230°.

(b) The filtrate from the above experiment began to precipitate more crystalline material on standing and was therefore evaporated to leave a white solid which was dissolved in hot water (3 ml), cooled (5°) and allowed to crystallise to give a white crystalline solid (121 mg) shown by $^1$H N.M.R. (DMSO) analysis to contain [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoate: β-cyclodextrin (1:1.5) complex.

EXAMPLE 2

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoate: γ-cyclodextrin (1:1.5) complex A solution of γ-cyclodextrin (1.09 g) in water (25 ml) was added to a solution of Compound A (0.20 g) in methanol (10 ml). The reaction solution was stirred at 21° for 26 h to produce a thick white suspension. The precipitate was filtered off and dried in vacuo to leave the title compound as a white solid (0.612 g), m.p.>310°, darkens above 250°.

Pharmaceutical Examples of Parenteral Injections/Infusions (i) Hydrochloride salt of Compound A equivalent to 50 mg base

| β-Cyclodextrin hydrate | 143 mg | 166 mg | 238 mg |
|---|---|---|---|
| Sodium hydroxide solution | to pH 7 | to pH 7 | to pH 7 |
| Water suitable for injection | to 50 ml | to 50 ml | to 50 ml |

The hydrochloride salt of Compound A was dissolved in 35 ml water suitable for injection and the β-cyclodextrin was added. This solution was titrated to pH7 with 0.02M sodium hydroxide solution and then adjusted to volume with water suitable for injection.

The solution may then be sterilised by filtration and filled into vials or ampoules.

(ii) Hydrochloride salt of Compound A equivalent to 50 mg base

| β-Cyclodextrin hydrate | 166 mg |
|---|---|
| Sodium chloride | 450 mg |
| pH 7.0 phosphate buffer | 2.5 ml |
| Sodium hydroxide solution | to pH 7 |
| Water suitable for injection | to 50 ml |

The hydrochloride salt of Compound A was dissolved in approximately 25 ml water suitable for injection. The β-cyclodextrin was dissolved therein and the resulting solution was titrated to pH6 with 0.02M sodium hydroxide solution and the phosphate buffer added. The sodium chloride was added to the solution and the pH adjusted to pH7 with sodium hydroxide. The solution was made up to volume with water suitable for injection. A sample of this solution was filled into a glass vial which was sealed with a rubber plug and metal overseal. This was then autoclaved.

(iii) Hydrochloride salt of Compound A Equivalent to 50 mg Base

| Hydroxypropyl-β-cyclodextrin | 170 mg |
|---|---|
| Mannitol | 2.5 g |
| pH 6.0 phosphate buffer | 5.0 ml |
| Sodium hydroxide solution | to pH 6 |
| Water suitable for injection | to 50 ml | the hydrochloride salt of Compound A was dissolved in approximately 25 ml water suitable for injection and the hydroxypropyl-β-cyclodextrin was added. The mannitol was then added and the solution titrated to pH 6 with 0.02M sodium hydroxide solution. The phosphate buffer solution was added and the solution adjusted to volume with water suitable for injection. The solution was then filtered and filled into glass vials which were sealed with rubber plugs and metal overseals. These were then autoclaved.

(iv) Hydrochloride Salt of Compound A Equivalent to 50 mg Base

| β-Cyclodextrin hydrate | 166 mg |
|---|---|
| Mannitol | 2.5 g |
| Sodium acid phosphate | 46 mg |
| Disodium phosphate, anhydrous | 5 mg |
| Sodium hydroxide solution | to pH 6 |
| Water suitable for injection | to 50 ml |

The hydrochloride salt of Compound A was dissolved in approximately 25 ml water suitable for injection. The β-cyclodextrin and mannitol were dissolved therein and the solution titrated to pH 6 with 0.02M sodium hydroxide solution. The sodium acid phosphate and anhydrous disodium phosphate were dissolved in water suitable for injection. This solution was added to the bulk solution which was made up to volume with water suitable for injection. The solution was filtered and filled into glass ampoules which were sealed and then autoclaved.

(v) Hydrochloride Salt of Compound A Equivalent to 50 mg Base

|  | Cyclodextrin | | |
| --- | --- | --- | --- |
|  | α | γ | Mixture β + γ |
| Cyclodextrin | 143 mg | 190 mg | 119 mg   136 mg |
| Mannitol | 2.5 g | 2.5 g | 2.5 g |
| pH 6.0 Phosphate buffer | 5.0 ml | 5.0 ml | 5.0 ml |
| Sodium hydroxide solution | to pH 6 | to pH 6 | to pH 6 |
| Water suitable for injection | to 50 ml | to 50 ml | to 50 ml |

The hydrochloride salt of Compound A was dissolved in approximately 25 ml water suitable for injection and the cyclodextrin(s) was (were) added. The mannitol was then added and the solution titrated to pH 6 with 0.02M sodium hydroxide solution. The phosphate buffer solution was added and the solution was adjusted to volume with water suitable for injection. The solution was then filtered and filled into glass vials which were sealed with rubber plugs and metal overseals.

Pharmaceutical Example of Oral Syrup

Hydrochloride Salt of Compound A Equivalent to 2.5 mg Base

| β-cyclodextrin hydrate | 9 mg |
| --- | --- |
| Citric acid | to pH 4.5 |
| Methyl hydroxybenzoate sodium | 5 mg |
| Propyl hydroxybenzoate sodium | 2 mg |
| Liquid orange flavour | qs |
| Sucrose | 3.25 g |
| Purified water | to 5.0 ml |

Dissolve the sucrose in a minimum quantity of water. Add the hydrochloride salt of Compound A and then the β-cyclodextrin with stirring; adjust the pH to 4.5 with citric acid. With continued stirring add a solution of the hydroxybenzoates and lastly the flavour. Adjust almost to volume with water and stir. Check the pH and adjust to 4.5 with citric acid if necessary. Make up to volume with water.

Pharmaceutical Example of Solution for Inhalation

Hydrochloride Salt of Compound A Equivalent to 2 Base

|  | Per 2 ml dose |
| --- | --- |
| β-cyclodextrin hydrate | 7 mg |
| Sodium chloride | 18 mg |
| Sodium hydroxide solution | to pH 7.2 |
| pH 7.2 phosphate buffer | 0.2 ml |
| Water suitable for injection | to 2 ml |

Dissolve the hydrochloride salt of Compound A in water suitable for injection. Dissolve the β-cyclodextrin therein and titrate the resulting solution to pH6 with sodium hydroxide solution; add the phosphate buffer solution. Add the sodium chloride and adjust to pH7.2 with sodium hydroxide solution. Make the solution up to volume with water suitable for injection and sterilize the solution by filtration. Fill aseptically into containers suitable for inhalation by nebulising.

We claim:

1. A clear aqueous formulation comprising the hydrochloride salt of [1R-[1α(Z),2β,3β,5α]]-(+)-7-[5-[[1,1'-biphenyl)-4-yl]methoxy]-3-hydroxy-2-(1-piperidinyl)-cyclopentyl]-4-heptenoic acid (Compound A) and β-cyclodextrin or a hydrate thereof, at a pH of about 6.0, wherein the formulation comprises about 1.4 moles of β-cyclodextrin for every 1 mole of the hydrochloride salt of Compound A and wherein the formulation comprises at least 1 mg./ml. of the salt of Compound A expressed as the free base.

2. A formulation as claimed in claim 1 which also comprises sodium hydroxide.

3. A method of treating occlusive vascular diseases and peri- and post-operative complications following organ transplantation, coronary artery bypass, peripheral artery bypass and thrombosis in a human or non-human animal body, which method comprises administering to said body a pharmaceutically effective amount of the formulation as claimed in claim 1.

* * * * *